(12) United States Patent
Bauer et al.

(10) Patent No.: US 6,426,078 B1
(45) Date of Patent: Jul. 30, 2002

(54) OIL IN WATER MICROEMULSION

(75) Inventors: Kurt Bauer, Freiburg-Tiengen; Clarissa Neuber, Villingen-Schwenningen; Axel Schmid, Gottmadingen-Bietingen; Karl Manfred Völker, Freiburg, all of (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/030,714

(22) Filed: Feb. 26, 1998

(30) Foreign Application Priority Data

Mar. 17, 1997 (CH) .............................................. 0628/97

(51) Int. Cl.[7] .......................... A61K 6/00; A61K 47/00; A61K 31/74
(52) U.S. Cl. .................. 424/401; 424/439; 424/78.03; 424/78.04; 514/844
(58) Field of Search ................. 424/401, 439, 424/78.03, 78.04, 455; 514/844

(56) References Cited

U.S. PATENT DOCUMENTS

| | | | |
|---|---|---|---|
| 4,835,002 A | 5/1989 | Wolf et al. | 426/590 |
| 5,045,337 A | 9/1991 | El-Nokaly et al. | 426/602 |
| 5,118,511 A * | 6/1992 | Horn et al. | 424/502 |
| 5,213,799 A * | 5/1993 | Goring et al. | 424/401 |

FOREIGN PATENT DOCUMENTS

| | | |
|---|---|---|
| GB | 2 222 770 | 3/1990 |
| GB | 2 297 759 | 8/1996 |

OTHER PUBLICATIONS

English language astract of JP 8120187.
Derwent Abstract No. AN 86–172070.
Patent Abstract of Japan No. JP 59051214.
Patent Abstract of Japan No. JP 07204487.
Derwent Abstract No. AN 87–040923.
Patent Abstract of Japan No. JP 09157159.
Patent Abstract of Japan No. JP 60137260.

* cited by examiner

Primary Examiner—Theodore J. Criares
Assistant Examiner—Jennifer Kim
(74) Attorney, Agent, or Firm—Byran Cave LLP

(57) ABSTRACT

The invention is concerned with a microemulsion of the oil-in water type, containing at least one polyglycerol ester as the emulsifier and at least one lipophilic substance as the internal phase.

The emulsifier contains a triglycerol monofatty acid ester and the lipophilic substance is one from the group carotenoids, especially, β-carotene, vitamins A, D, E and K and their derivatives and polyunsaturated fatty acids.

55 Claims, No Drawings

OIL IN WATER MICROEMULSION

The invention is concerned with a microemulsion of the oil-in-water type, containing at least one polyglycerol ester as the emulsifier and at least one lipophilic substance as the internal phase.

Certain substances, which can be used for the manufacture of a microemulsion, lead to microemulsions which can be used without hesitation in foodstuffs or in the pharmaceutical or cosmetic field for human beings. For example, in the pharmaceutical field microemulsions have been manufactured using tensides as emulsifiers, which contain polyoxyethylene residues in the hydrophilic part of the chain. With the aid of these tensides even fat-soluble substances, such as e.g. vitamins or pharmaceutically active substances, can be solubilized in water to give a clear emulsion. However, these emulsifiers can be harmful to health. Use in foodstuffs is accordingly prohibited, mainly because these tensides contain residual monomers which are potentially carcinogenic.

Great Britain Patent Publication GB 2,222,770 describes microemulsions having sugar esters as emulsifiers, which contain as essential co-emulsifiers low-molecular polyoxyethylenes which are, however, toxic.

U.S. Pat. No. 5,045,337 describes for the foodstuff field, a water-in-oil microemulsion system with polyglycerol esters or mono-diglycerides as emulsifiers for the formulation of hydrophilic vitamins and flavorants.

U.S. Pat. No. 4,835,002 describes oil-in-water microemulsions with polyglycerol esters for the formulation of lipophilic edible oils, fragrance-imparting oils or flavor-imparting oils, which are proposed for the foodstuff field.

The present invention is concerned with an oil in water microemulsion which comprises as an emulsifier, at least one polyglycol ester, the polyglycol ester being a triglycerol monofatty acid ester; at least one lipophilic substance selected from the group consisting of carotenoids, vitamin A and its derivatives, vitamin D and its derivatives, vitamin E and its derivatives, vitamin K and its derivatives, and polyunsaturated fatty acids, and combinations thereof; and water.

The microemulsion is characterized in that the emulsifier contains at least one triglycerol monofatty acid ester and the lipophilic substance is selected from the group of carotenoids, especially β-carotene, vitamins A, D, E and K and their derivatives and polyunsaturated fatty acids such as e.g. arachidonic acid, eicosapentaenoic acid and docosahexaenoic acid.

Derivatives of the vitamins are, for example, vitamin A acetate, vitamin A palmitate, vitamin E acetate and the like. Under vitamin E there is to be understood synthetic of naturals tocopherols.

With this microemulsion it is possible to solubilize the afore-mentioned lipophilic substances in any amount of water without changing the microscopic appearance of the microemulsion or without breaking the microemulsion.

The emulsifiers used are non-toxic and, accordingly, such microemulsions can be used in foodstuffs. They can also be used in the pharmaceutical field. Cosmetic formulations are likewise possible.

Preferred triglycerol monofatty acid esters are triglycerol monolaurate, triglycerol monocaproate or triglycerol monocaprylate, especially triglycerol monolaurate or triglycerol monocaprylate.

The microemulsions can be manufactured with or without a co-emulsifier. Preferred co-emulsifiers are ethanol, propylene glycol, transcutol (diethylene gylcol monoethyl ether, available from Gattefosse S.A., France), polyethylene glycols, polyglycerols, monoglycerides or lecithin, especially transcutol, monoglycerides or lecithin, with lecithin being especially preferred.

Furthermore, the microemulsion can also contain at least one carrier oil. The lipophilic substance is dissolved at least in part in the carrier oil, which increases the final content of lipophilic substance in the finished microemulsion. The carrier oil is preferably orange oil, palm oil, a triglyceride, squalane, squalene, limonene, isopropyl myristate or isopropyl palmitate, especially orange oil, squalane or limonene, preferably orange oil.

The microemulsion contains as the vitamin especially tocopherol and/or vitamin A, especially vitamin A palmitate.

As the carotenoid the microemulsion preferable contains all-trans-β-carotene, 9-cis-β-carotene, 13-cis-β-carotene, β-opo-8'-carotenic acid ethyl ester, apocarotenal, astaxanthin, canthaxanthin, crocetin or lycopene. A β-carotene is especially preferred.

Preferably, the amount of lipophilic substance, for example tocopherol, lies at 1–20 wt. %, the amount of emulsifier lies at 10–99 wt. % and the amount of co-emulsifier (when present) lies at 1–89 wt. %, with the ratio of emulsifier to co-emulsifier preferably being 50:50 wt. %.

The microemulsion can be used especially in foodstuffs, in pharmaceutical preparations and in cosmetics.

For foodstuffs, the oil in water microemulsions of the present invention provide a convenient way to add or fortify a variety of foodstuffs, for examples, beverages, baked goods, dressing, and the like, with the lipophilic substances mentioned herein. The same holds true for pharmaceutical compositions and cosmetics. For pharmaceutical compositions, the oil in water microemulsions permit the addition of the lipophilic substance to pharmaceutical compositions, for example, oral vitamin solutions. For cosmetics, the oil in water microemulsions permits the addition of the lipophilic substances to variety of cosmetics, for example, foundation, lipstick, and the like.

In each instance for foodstuff, pharmaceutical, and cosmetic materials, the addition of the lipophilic substances mentioned herein provide valuable properties to the materials as one of ordinary skill in the art will appreciate when such lipophilic substances are either consumed (foodstuffs or pharmaceuticals) or are topically applied (pharmaceuticals or cosmetics). For the various foodstuff, pharmaceutical and cosmetic materials, the amounts of oil in water microemulsion to be added will depend upon the amount of lipophilic substance that is desired to be added to the material and the effect which the lipophilic substance is to have, for example, antioxidant effect or intaking the recommended daily allowance of the lipophilic substances.

In the case of foodstuffs, by fortifying the foodstuffs with the oil in water microemulsion of the present application, the lipophilic substance incorporated by use of the microemulsion provides for levels of the lipophilic substance which would be greater than that present in the foodstuff without the addition of the microemulsion. In the case of cosmetics, by adding the microemulsion of the present invention, the cosmetics can be fortified with many of the lipophilic substances which are considered useful in treating wrinkles, burns, etc. In the case of pharmaceuticals, using the microemulsions of the present invention permits valuable formulations to be fortified with, for example, the lipophilic substances mentioned herein to make vitamin solutions and other medicaments to be prepared.

The microemulsion in accordance with the invention is especially suitable for formulations in which the aforementioned lipophilic substances need to be solubilized as lipophilic pharmaceutically active substances. Thus, tocopherol is especially useful as the lipid.

The microemulsion is dilutable or miscible with water in any ratio. A pharmaceutically convenient dilution of the microemulsion contains e.g. 90 wt. % water. In this formulation 0.1–2 wt. % tocopherol would then be present.

The speed of the microemulsion formation depends on the velocity at which the individual components dissolve. When e.g. salve-like emulsifiers, such as, for example, triglycerol monolaurate, are used, the speed at which these emulsifiers dissolve can be accelerated by slight stirring and possibly warming to about 40–45° C. A magnetic stirrer is suitable for this purpose. However, a different stirrer or any heating system can be used. The formulation is finished when a clear, isotropic liquid has formed from the individual components, which usually occurs after several minutes.

The formulations can additionally contain flavorants, colorants and/or thickeners when their use requires this to be the case. If the content of polyglycerol esters amounts to less than about 3–5%, the formulation can be additionally preserved with conventional preservatives.

Further features and particulars will be evident from the following Examples.

EXAMPLE 1

5 g of tocopherol were weighed out together with 30 g of triglycerol monolaurate as well as 65 g of demineralized water and dissolved at 45–50° C. while stirring. There was obtained a clear, isotropic emulsion which was stable between 4° C. and 45° C. This can be diluted with any amount of water.

EXAMPLE 2

1 g of tocopherol was stirred with 4.5 g of triglycerol monolaurate and 4.5 g of ethanol. A clear, yellow microemulsion was obtained at room temperature. This can be diluted with any amount of water without breaking.

EXAMPLE 3

1 g of tocopherol was stirred at room temperature with 4.5 g of triglycerol monolaurate and 4.5 g of propylene glycol. A yellow, viscous solution was obtained. The resulting microemulsion can be diluted with more than 100 ml of water without breakage of the microemulsion.

EXAMPLE 4

2.5 g of tocopherol and 7.5 g of triglycerol monocaprylate were stirred at room temperature using a magnetic stirrer until a clear microemulsion base was obtained. This base can be diluted with water and then forms microemulsions of the o/w type.

EXAMPLE 5

0.6 g of phytomenadione (vitamin K1), 2.35 g of lecithin (co-emulsifier) and 7.05 g of triglycerol monocaprylate were stirred at room temperature using a magnetic stirrer until a clear microemulsion base was obtained. This base can be diluted with water and then forms microemulsions of the o/w type.

EXAMPLE 6

1 g of tocopherol was stirred at room temperature with 9 g of triglycerol monocaproate. The resulting clear, yellow microemulsion was miscible with water in any ratio without breaking the microemulsion.

EXAMPLE 7

1.6 g of orange oil (carrier oil) were weighed out together with 3.0 g of triglycerol monolaurate (emulsifier) and 5.4 g of demineralized water and dissolved within a few minutes while stirring. A transparent yellow microemulsion base was obtained. 37 mg of β-apo-8'-carotenic acid ethyl ester were added to this microemulsion base. The carotenoid was dissolved in the microemulsion base within a few hours while stirring. There was obtained a clear, red microemulsion which was miscible with any amount of water.

EXAMPLE 8

1.6 of orange oil (carrier oil) were weighed out together with 3.0 g of triglycerol monolaurate (emulsifier) and 5.4 g of demineralized water and dissolved within a few minutes while stirring. 31 mg of β-apo-8'-carotenal were added to this microemulsion base. The carotenoid was dissolved in the microemulsion base within a few hours while stirring. There was obtained a clear, red microemulsion which was miscible with any amount of water.

EXAMPLE 9

1.6 g of orange oil (carrier oil) were weighed out together with 3.0 g of triglycerol monolaurate (emulsifier) and 5.4 g of demineralized water and dissolved within a few minutes while stirring. 0.3 mg of astaxanthin was added to this microemulsion base. The carotenoid was dissolved in the microemulsion base within a few hours while stirring. There was obtained a clear, orange colored microemulsion which was miscible with any amount of water.

EXAMPLE 10

1.6 g of orange oil (carrier oil) were weighed out together with 3.0 g of triglycerol monolaurate (emulsifier) and 5.4 g of demineralized water and dissolved within a few minutes while stirring. 1 mg of canthaxanthin was added to this microemulsion base. The carotenoid was dissolved in the microemulsion base within a few hours while stirring. There was obtained a clear, orange colored microemulsion which was miscible with any amount of water.

EXAMPLE 11

1.6 g of orange oil (carrier oil) were weighed out together with 3.0 g of triglycerol monolaurate (emulsifier) and 5.4 g of demineralized water and dissolved within a few minutes while stirring. 8 mg of lycopene were added to this microemulsion base. The carotenoid was dissolved in the microemulsion base within a few hours while stirring. There was obtained a clear, red microemulsion which was miscible with any amount of water.

EXAMPLE 12

1.6 g of orange oil (carrier oil) were weighed out together with 3.0 g of triglycerol monolaurate (emulsifier) and 5.4 g of demineralized water and dissolved within a few minutes while stirring. 2 mg of all-trans-β-carotene were added to this microemulsion base. The carotenoid was dissolved in the microemulsion base within a few hours while stirring. There was obtained a clear, orange-red microemulsion which was miscible with any amount of water.

EXAMPLE 13

1.6 g of orange oil (carrier oil) were weighed out together with 3.0 g of triglycerol monolaurate (emulsifier) and 5.4 g of demineralized water and dissolved within a few minutes while stirring. 30 mg of 13-cis-β-carotene were added to this microemulsion base. The carotenoid was dissolved in the microemulsion base within a few hours while stirring. There was obtained a clear, red microemulsion which was miscible with any amount of water.

EXAMPLE 14

1.6 g of orange oil (carrier oil) were weighed out together with 3.0 g of triglycerol monolaurate (emulsifier) and 5.4 g of demineralized water and dissolved within a few minutes while stirring. 90 mg of 9-cis-β-carotene were added to this microemulsion base. The carotenoid was dissolved in the microemulsion base within a few hours while stirring. There was obtained a clear, red microemulsion which was miscible with any amount of water.

EXAMPLE 15

0.6 g of vitamin A acetate and 9.4 g of triglycerol monolaurate (emulsifier) were treated with 15.0 g of demineralized water and warmed to 60° C. within about 5 min. while stirring using a magnetic stirrer. After cooling there was obtained a yellow microemulsion which was dilutable with any amount of water.

EXAMPLE 16

1.0 g of vitamin E acetate, 8.0 g of triglycerol monolaurate (emulsifier) and 1.0 g of Imwitor 988 (caprylic acid monodiglyceride available from Hüls; co-emulsifier) were stirred at room temperature with 10.0 g of demineralized water using a magnetic stirrer until a microemulsion was obtained. This microemulsion was dilutable with any amount of water.

What is claimed is:

1. An oil in water microemulsion comprising:
   (a) a triglycerol monofatty acid ester emulsifier selected from the group consisting of triglycerol monolaurate, triglycerol monocaproate, and triglycerol monocaprylate, the emulsifier being present in an amount of from about 10 to about 99 wt %;
   (b) a lipophilic substance selected from the group consisting of carotenoids, vitamin A and its derivatives, vitamin D and its derivatives, vitamin E and its derivatives, vitamin K and its derivatives, and polyunsaturated fatty acids, and combinations thereof, the lipophilic substance being present in an amount of from about 1 to about 20 wt %; and
   (c) water, wherein the microemulsion that is formed is stable.

2. The oil in water microemulsion of claim 1 which further contains a co-emulsifier.

3. The oil in water microemulsion of claim 2 which further contains at least one carrier oil.

4. The oil in water mircoemulsion of claim 1 wherein the triglycerol monofatty acid ester is selected from triglycerol monolaurate or triglycerol monocaprylate.

5. The oil in water microemulsion of claim 2, wherein the co-emulsifier is selected from ethanol, propylene glycol, transcutol, polyethylene glycol, polyglycerol, monoglyceride, or lecithin.

6. The oil in water microemulsion of claim 5, wherein the co-emulsifier is selected from transcutol, monoglyceride, or lecithin.

7. The oil in water microemulsion of claim 6, wherein the co-emulsifier is lecithin.

8. The oil in water microemulsion of claim 5, wherein the triglycerol monofatty acid ester is selected from triglycerol monolaurate, triglycerol monocaproate, or triglycerol monocaprylate.

9. The oil in water microemulsion of claim 1 which further contains a carrier oil.

10. The oil in water microemulsion of claim 9 wherein the carrier oil is selected form the orange oil, palm oil, a triglyceride, squalene, limonene, isopropyl myristate, or isopropyl palmitate.

11. The oil in water microemulsion of claim 10, wherein the carrier oil is selected from orange oil, squalane, or limonene.

12. The oil in water microemulsion of claim 11, wherein the carrier oil is orange oil.

13. The oil in water microemulsion of claim 3, wherein the carrier oil is selected from orange oil, palm oil, a triglyceride, squalene, squalane, limonene, isopropyl myristate, or isopropyl palmitate.

14. The oil in water microemulsion of claim 13, wherein the carrier oil is selected from orange oil, squalane, or limonene.

15. The oil in water microemulsion of claim 14, wherein the carrier oil is orange oil.

16. The oil in water microemulsion of claim 1, wherein the lipophilic substance is selected from vitamin A and its derivatives, vitamin E and its derivatives, or combinations thereof.

17. The oil in water microemulsion of claim 16, wherein the lipophilic substance is selected from vitamin A, vitamin A palmitate, and vitamin A acetate.

18. The oil in water microemulsion of claim 2, wherein the lipophilic substance is selected from vitamin A and its derivatives, vitamin E and its derivatives, or combinations thereof.

19. The oil in water microemulsion of claim 18, wherein the lipophilic substance is selected from vitamin A, vitamin A palmitate, and vitamin A acetate.

20. The oil in water microemulsion of claim 9 wherein the lipophilic substance is selected from vitamin A and its derivatives, vitamin E and its derivatives, or combinations thereof.

21. The oil in water microemulsion of claim 20, wherein the lipophilic substance is selected from vitamin A, vitamin A palmitate, and vitamin A acetate.

22. The oil in water microemulsion of claim 3, wherein the lipophilic substance is selected from vitamin A and its derivatives, vitamin E and its derivatives, or combinations thereof.

23. The oil in water microemulsion of claim 22, wherein the lipophilic substance is selected from vitamin A, vitamin A palmitate, and vitamin A acetate.

24. The oil in water microemulsion of claim 1, wherein the lipophilic substance is a carotenoid.

25. The oil in water microemulsion of claim 24, wherein the carotenoid is selected from the group of all-trans-β-carotene, 9-cis-β-carotene, 13-cis-β-carotene, β-apo-8'-carotenic acid ethyl ester, apocarotenal, astaxanthin, canthaxanthin, crocetin, and lycopene.

26. The oil in water microemulsion of claim 25, wherein the carotenoid is selected from the group of all-trans-β-carotene, 9-cis-β-carotene, and 13-cis-β-carotene.

27. The oil in water microemulsion of claim 2, wherein the lipophilic substance is a carotenoid.

28. The oil in water microemulsion of claim 27, wherein the carotenoid is selected from the group of all-trans-β-carotene, 9-cis-β-carotene, 13-cis-β-carotene, β-apo-8'- carotenic acid ethyl ester, apocarotenal, astaxanthin, canthaxanthin, crocetin, and lycopene.

29. The oil in water microemulsion of claim 28, wherein the carotenoid is selected from the group of all-trans-β-carotene, 9-cis-β-carotene, and 13-cis-β-carotene.

30. The oil in water microemulsion of claim 9 wherein the lipophilic substance is a carotenoid.

31. The oil in water microemulsion of claim 30, wherein the carotenoid is selected from the group of all-trans-β-carotene, 9-cis-β-carotene, 13-cis-β-carotene, β-apo-8'-carotenic acid ethyl ester, apocarotenal, astaxanthin, canthaxanthin, crocetin, and lycopene.

32. The oil in water microemulsion of claim 31, wherein the carotenoid is selected from the group of all-trans-β-carotene, 9-cis-β-carotene, and 13-cis-β-carotene.

33. The oil in water microemulsion of claim 3, wherein the lipophilic substance is a carotenoid.

34. The oil in water microemulsion of claim 33, wherein the carotenoid is selected from the group of all-trans-β-carotene, 9-cis-β-carotene, 13-cis-β-carotene, β-apo-8'-carotenic acid ethyl ester, apocarotenal, astaxanthin, canthaxanthin, crocetin, and lycopene.

35. The oil in water microemulsion of claim 34, wherein the carotenoid is selected from the group of all-trans-β-carotene, 9-cis-β-carotene, and 13-cis-β-carotene.

36. The oil in water microemulsion of claim 2 which is further diluted with water.

37. The oil in water microemulsion of claim 9 which is further diluted with water.

38. The oil in water microemulsion of claim 3 which is further diluted with water.

39. The oil in water microemulsion of claim 1, which further contains a co-emulsifier in an amount of from about 1 to about 89 wt %.

40. The oil in water microemulsion of claim 39, wherein the emulsifier and co-emulsifier are present in a ratio of about 50:50 wt %.

41. The oil in water microemulsion of claim 40, wherein the lipophilic substance vitamin E and its derivatives.

42. The oil in water microemulsion of claim 40, wherein the lipophilic substance is a carotenoid.

43. The oil in water microemulsion of claim 42, wherein the carotenoid is selected from the group of all-trans-β-carotene, 9-cis-β-carotene, 13-cis-β-carotene, β-apo-8'-carotenic acid ethyl ester, apocarotenal, astaxanthin, canthaxanthin, crocetin, and lycopene.

44. The oil in water microemulsion of claim 40, wherein the lipophilic substance is vitamin A and its derivatives.

45. The oil in water microemulsion of claim 1 which is further diluted with water.

46. The oil in water microemulsion of claim 39 which is further diluted with water.

47. A fortified foodstuff comprising:
(a) a foodstuff; and
(b) an oil in water microemulsion comprising:
    (i) a triglycerol monofatty acid ester emulsifier selected from the group consisting of triglycerol monolaurate, triglycerol monocaproate, and triglycerol monocaprylate, the emulsifier being present in an amount of from about 10 to about 99 wt %;
    (ii) a lipophilic substance selected from the group consisting of carotenoids, vitamin A and its derivatives, vitamin D and its derivatives, vitamin E and its derivatives, vitamin K and its derivatives, polyunsaturated fatty acids, and combinations thereof, the lipophilic substance being present in an amount of from about 1 to about 20 wt %; and
    (iii) water, wherein the microemulsion that is formed is stable.

48. The forfified of claim 47, wherein the oil in water microemulsion further contains a co-emulsifier.

49. The fortified of claim 48, wherein the oil in water microemulsion further contains a carrier oil.

50. A fortified cosmetic comprising:
(a) a cosmetic; and
(b) an oil in water microemulsion comprising:
    (i) a triglycerol monofatty acid ester emulsifier selected from the group consisting of triglycerol monolaurate, triglycerol monocaproate, and triglycerol monocaprylate, the emulsifier being present in an amount of from about 10 to about 99 wt %;
    (ii) a lipophilic substance selected from the group consisting of carotenoids, vitamin A and its derivatives, vitamin D and its derivatives, vitamin E and its derivatives, vitamin K and its derivatives, polyunsaturated fatty acids, and combinations thereof, the lipophilic substance being present in an amount of from about 1 to about 20 wt %; and
    (iii) water, wherein the microemulsion that is formed is stable.

51. The fortified cosmetic of claim 50, wherein the oil in water microemulsion further contains a co-emulsifier.

52. The fortified cosmetic of claim 51, wherein the oil in water microemulsion further contains a carrier oil.

53. A fortified pharmaceutical composition comprising:
(a) a pharmaceutical composition; and
(b) an oil in water microemulsion comprising:
    (i) at least one triglycerol monofatty acid ester emulsifier selected from the group consisting of triglycerol monolaurate, triglycerol monocaproate, and triglycerol monocaprylate;
    (ii) at least one lipophilic substance in an amount of from about 1% to about 20% (wt) selected from the group consisting of carotenoids, vitamin A and its derivatives, vitamin D and its derivatives, vitamin E and its derivatives, vitamin K and its derivatives, polyunsaturated fatty acids, and combinations thereof; and
    (iii) water, wherein the microemulsion that is formed is stable.

54. The fortified pharmaceutical composition of claim 53, wherein the oil in water microemulsion further contains a co-emulsifier.

55. The fortified pharmaceutical composition of claim 54, wherein the oil in water microemulsion further contains a carrier oil.

* * * * *

UNITED STATES PATENT AND TRADEMARK OFFICE
CERTIFICATE OF CORRECTION

PATENT NO. : 6,426,078 B1  Page 1 of 1
DATED : July 30, 2002
INVENTOR(S) : Kurt Bauer et al.

It is certified that error appears in the above-identified patent and that said Letters Patent is hereby corrected as shown below:

Column 6,
Line 8, please change "form" to -- form --;

Column 7,
Line 39, after "substance" please insert -- is --;

Column 8,
Line 10, please change "forfified" to -- fortified foodstuff --;
Line 12, after "fortified" please insert -- foodstuff --.

Signed and Sealed this

Twelfth Day of November, 2002

Attest:

JAMES E. ROGAN
Attesting Officer  Director of the United States Patent and Trademark Office